(12) United States Patent
Tribble et al.

(10) Patent No.: US 10,810,323 B2
(45) Date of Patent: *Oct. 20, 2020

(54) WELLNESS REGISTRY

(71) Applicant: Apple Inc., Cupertino, CA (US)

(72) Inventors: Guy L. Tribble, Hillsborough, CA (US); Afshad M. Mistri, Mountain View, CA (US); Anton M. Davydov, Gilroy, CA (US); Zachery Kennedy, San Jose, CA (US); Zachury Minjack, San Francisco, CA (US); Dennis S. Park, San Francisco, CA (US); Dylan Ross Edwards, San Jose, CA (US); Adam L. Beberg, San Jose, CA (US)

(73) Assignee: Apple Inc., Cupertino, CA (US)

( * ) Notice: Subject to any disclaimer, the term of this patent is extended or adjusted under 35 U.S.C. 154(b) by 317 days.

This patent is subject to a terminal disclaimer.

(21) Appl. No.: 15/885,448

(22) Filed: Jan. 31, 2018

(65) Prior Publication Data

US 2018/0157864 A1  Jun. 7, 2018

Related U.S. Application Data

(63) Continuation of application No. 15/167,699, filed on May 27, 2016, now Pat. No. 9,916,474, which is a
(Continued)

(51) Int. Cl.
*G06F 21/62* (2013.01)
*G06F 16/9535* (2019.01)
(Continued)

(52) U.S. Cl.
CPC ...... *G06F 21/6254* (2013.01); *G06F 16/9535* (2019.01); *G16H 10/20* (2018.01); *G16H 10/60* (2018.01); *G16H 10/65* (2018.01)

(58) Field of Classification Search
CPC ........ G16H 10/60; G16H 10/65; G16H 40/67; G16H 40/20; G16H 10/20; G06Q 50/24;
(Continued)

(56) References Cited

U.S. PATENT DOCUMENTS 5,515,344 A   5/1996 Ng
6,600,696 B1  7/2003 Lynn
(Continued)

FOREIGN PATENT DOCUMENTS

CN   101107619 A   1/2008
CN   102790761 A   11/2012
(Continued)

OTHER PUBLICATIONS

Office Action received for Australian Patent Application No. 2018201260, dated Jul. 17, 2019, 3 pages.
(Continued)

*Primary Examiner* — Maroun P Kanaan
(74) *Attorney, Agent, or Firm* — Dentons US LLP

(57) ABSTRACT

The present disclosure relates to receiving and sharing wellness data. The wellness data can be received by a user device from any number of sensors external or internal to the user device, from a user manually entering the wellness data, or from other users or entities. The user device can securely store the wellness data on the user device and transmit the wellness data to be stored on a remote database. A user of the device can share some or all of the wellness data with research entities conducting research studies, friends, relatives, caregivers, healthcare providers, or the like.

36 Claims, 6 Drawing Sheets

Related U.S. Application Data continuation of application No. PCT/US2013/073188, filed on Dec. 4, 2013.

(51) Int. Cl.
  *G16H 10/60* (2018.01)
  *G16H 10/65* (2018.01)
  *G16H 10/20* (2018.01)

(58) Field of Classification Search
  CPC ............ G06F 19/3418; G06F 16/9535; G06F 19/3481; G06F 16/2455; G06F 16/951; G06F 19/3456; G06F 21/6254
  See application file for complete search history.

(56) References Cited

U.S. PATENT DOCUMENTS

| | | | |
|---|---|---|---|
| 6,950,839 | B1 | 9/2005 | Green et al. |
| 7,166,078 | B2 | 1/2007 | Saini et al. |
| 2001/0039503 | A1 | 11/2001 | Chan et al. |
| 2003/0126114 | A1* | 7/2003 | Tedesco .............. G06F 16/2455 |
| 2004/0193069 | A1 | 9/2004 | Takehara |
| 2005/0027208 | A1 | 2/2005 | Shiraishi et al. |
| 2005/0149362 | A1 | 7/2005 | Peterson et al. |
| 2005/0187794 | A1 | 8/2005 | Kimak |
| 2008/0005106 | A1 | 1/2008 | Schumacher et al. |
| 2008/0021884 | A1* | 1/2008 | Jones .................... G06F 16/951 |
| 2008/0172773 | A1 | 7/2008 | Chatman et al. |
| 2008/0243885 | A1 | 10/2008 | Harger et al. |
| 2009/0240521 | A1 | 9/2009 | Simons et al. |
| 2010/0312138 | A1 | 12/2010 | Regas |
| 2011/0010195 | A1 | 1/2011 | Cohn |
| 2011/0119088 | A1 | 5/2011 | Gunn |
| 2011/0166631 | A1 | 7/2011 | Breining |
| 2012/0023586 | A1 | 1/2012 | Flickner et al. |
| 2012/0185267 | A1 | 7/2012 | Kamen et al. |
| 2013/0262155 | A1 | 10/2013 | Hinkamp |
| 2013/0268398 | A1 | 10/2013 | Agami et al. |
| 2013/0304510 | A1 | 11/2013 | Chen et al. |
| 2013/0325511 | A1 | 12/2013 | Neagle, III |
| 2014/0046926 | A1* | 2/2014 | Walton .................... G06F 16/20 707/710 |
| 2016/0106398 | A1 | 4/2016 | Kuppuswami |
| 2016/0275310 | A1 | 9/2016 | Tribble et al. |
| 2017/0150917 | A1 | 6/2017 | Brief et al. |
| 2017/0235443 | A1 | 8/2017 | Suzuki |
| 2017/0258455 | A1 | 9/2017 | Qi |
| 2017/0319184 | A1 | 11/2017 | Sano |
| 2018/0055490 | A1 | 3/2018 | Lee et al. |
| 2019/0223843 | A1 | 7/2019 | Vitti |

FOREIGN PATENT DOCUMENTS

| | | | |
|---|---|---|---|
| KR | 10-2013-0093837 A | 8/2013 |
| WO | 2001/96986 A2 | 12/2001 |

OTHER PUBLICATIONS

Notice of Allowance received for Chinese Patent Application No. 201380081315.7, dated Jan. 4, 2019, 2 pages (1 page of English Translation and 1 page of Official Copy).
Notice of Acceptance received for Australian Patent Application No. 2013406817, dated Nov. 21, 2017, 3 pages.
EPO, "Mitteilung des Europaischen Patentamts vom 1. oktober 2007 uber Geschaftsmethoden = Notice from the European Patent Office dated Oct. 1, 2007 concerning business methods", Journal Officiel De LOffice Europeen Des Brevets.Official Journal of the European Patent Office.Amtsblattt Des Europaeischen, vol. 38, No. 11, Nov. 2007, pp. 592-593.
Final Office Action received for U.S. Appl. No. 15/167,699, dated Jun. 30, 2017, 8 Pages.
International Preliminary Report on Patentability received for PCT Patent Application No. PCT/US2013/073188, dated Jun. 16, 2016, 6 pages.
International Search Report and Written Opinion received for PCT Patent Application No. PCT/US2013/073188 dated Feb. 24, 2014, 8 pages.
Non-Final Office Action received for U.S. Appl. No. 15/167,699, dated Oct. 21, 2016, 13 pages.
Notice of Allowance received for U.S. Appl. No. 15/167,699, dated Oct. 27, 2017, 8 pages.
Office Action received for Australian Patent Application No. 2013406817, dated Aug. 1, 2017, 3 pages.
Office Action received for Australian Patent Application No. 2013406817, dated Nov. 14, 2016, 4 pages.
"Statement in Accordance With the Notice from the European Patent Office dated Oct. 1, 2007 Concerning Business Methods Pct Declaration Conformement Au Communique De L'office Europ", XP002456414, Nov. 2007.
Notice of Acceptance received for Australian Patent Application No. 2018201260, dated Jan. 15, 2020, 3 pages.
Notice of Allowance received for Korean Patent Application No. 10-2018-7032096, dated Dec. 12, 2018, 4 pages (1 page of English Translation and 3 pages of Official copy).
Myflo App, "Functional Medicine Period Tracker and Hormone Balancing App", Available online at <https://web.archive.org/web/20170127104125/https://myflotracker.com/>, Jan. 2017, 14 pages.
Myflo Tutorial, "How to change the start date of your current period", Available online at <https://www.youtube.com/watch?v=uQQ-odIBJB4>, Jan. 23, 2017, 3 pages.
Myflo Tutorial, "Setting and changing the end date of your period", Available online at <https://www.youtube.com/watch?v=UvAA4OgqL3E>, Jan. 23, 2017, 3 pages.
Office Action received for Australian Patent Application No. 2018201260, dated Feb. 12, 2019, 6 pages.
Office Action received for Australian Patent Application No. 2018201260, dated Sep. 5, 2019, 5 pages.
Office Action received for Indian Patent Application No. 201617016494, dated Apr. 27, 2020, 7 pages.
Notice of Allowance received for Korean Patent Application No. 10-2016-7014353, dated Aug. 2, 2018, 3 pages (Official Copy Only) (See Communication under 37 CFR § 1.98(a) (3)).
Office Action received for Chinese Patent Application No. 201380081315.7, dated Aug. 16, 2018, 6 pages (3 pages of English Translation and 3 pages of Official Copy).
Office Action received for Chinese Patent Application No. 201380081315.7, dated Mar. 2, 2018, 12 pages (5 pages of English Translation and 7 pages of Official Copy).
Office Action received for European Patent Application No. 13812320.3, dated Mar. 28, 2018, 7 pages
Office Action received for Korean Patent Application No. 10-2016-7014353, dated Mar. 21, 2018, 11 pages (5 pages of English Translation and 6 pages of Official Copy).
Weiyu et al., "A Multi-identities Authentication and Authorization Schema in Cloud Computing", Aug. 20, 2012, pp. 7-10 (English Abstract Submitted).

\* cited by examiner

1

WELLNESS REGISTRY

CROSS-REFERENCE TO RELATED APPLICATION

This application is a continuation of U.S. application Ser. No. 15/167,699, filed on May 27, 2016, which is a continuation of PCT/US2013/073188, filed on Dec. 4, 2013. The contents of which are incorporated herein by reference.

FIELD

The following disclosure relates generally to data management and, more specifically, to sharing wellness data.

BACKGROUND

Approximately 133 million Americans currently suffer from at least one chronic condition. This number is expected to rise to approximately 165 million by the year 2020. As a result, the cost of healthcare in the United States is expected to increase dramatically. Attempts have been made to improve the health of individuals by providing them with tools to monitor and track their wellness data. Wellness data can generally include any type of data associated with a person's health, such as their weight, heart rate, blood pressure, blood glucose level, medication compliance, activity level, or the like. Users can monitor their wellness using devices, such as blood pressure cuffs, blood glucose monitors, electrocardiograms, step counters, and the like. Software applications (e.g., Apps) associated with each of these devices have also been developed to allow users to track their wellness data over time. While each application can be used to view useful information about a user's health, current applications are limited in their ability to allow users to store, view, and share wellness data collected by different devices.

SUMMARY

The present disclosure relates to processes for sharing wellness data. One example process may include receiving, from a plurality of user devices, wellness data authorized for storage to a database of wellness data; storing the wellness data in the database of wellness data; receiving, from a research entity, a request to access the database of wellness data; approving the request to access the database of wellness data; receiving, from the research entity, a request to perform a search query on the database of wellness data; performing the search query on the database of wellness data; and transmitting results of the search query to the research entity.

In some examples, the wellness data is associated with a plurality of users, and wherein an authorization to include the wellness data in the database of wellness data was received from each of the plurality of users prior to the wellness data being stored in the database of wellness data.

In some examples, the process may further include receiving wellness data of two or more users; and storing the received wellness data of the two or more users in the database of wellness data. In other examples, the process may further include receiving, before storing the received wellness data of the two or more users in the database of wellness data, an authorization from each of the two or more users to include the received wellness data in the database of wellness data.

In some examples, the process may further include receiving wellness data of two or more users; and excluding the received wellness data of the two or more users from the database of wellness data absent an authorization from each of the two or more users that their wellness data is to be included in the database of wellness data.

In some examples, the process may further include wellness data of two or more users, wherein the wellness data of each of the two or more users is received from a wellness database located on a user device of each user.

In some examples, the process may further include updating the database of wellness data by receiving one of intermittent and continuous updates from the wellness database located on each user's user device.

In some examples, the database of wellness data comprises metadata associated with the wellness data, wherein the metadata comprises a time the wellness data was recorded, a type of the wellness data, and a device used to record the wellness data.

In some examples, the database of wellness data comprises wellness data from a plurality of users. In other examples, the process may further include receiving, prior to performing the search query, authorization from two or more users of the plurality of users to authorize their wellness data to be searchable. In yet other examples, the process may further include denying a search query on wellness data from the plurality of users absent authorization that their wellness data is to be searchable.

In some examples, the wellness data is stored in the database of wellness data anonymously.

Another example process may include receiving, from a plurality of user devices, wellness data authorized for storage to a database of wellness data; storing the wellness data in the database of wellness data; receiving, by a server, an authorization from a user to provide access to at least a portion of the user's wellness data in the database of wellness data; and providing access to the at least a portion of the user's wellness data in the database of wellness data based on the authorization.

In some examples, the authorization authorizes entities to perform search queries on the at least a portion of the user's wellness data.

In some examples, the authorization is received in response to a request made by a querying entity. In other examples, the request comprises a selectable link transmitted to a user device of the user, and wherein the authorization is transmitted to the server in response to a selection of the link. In yet other examples, the selectable link is displayed in an application associated with a type of wellness data on the user's user device.

In some examples, the authorization authorizes an entity conducting a research study to access the at least a portion of the user's wellness data. In other examples, the authorization is transmitted to the server in response to the user selecting the research study from a list of research studies displayed on a user device of the user.

In some examples, the process may further include receiving, by the server, data associated with research studies of interest to the user; monitoring a plurality of research studies; and transmitting a notification to a user device of the user in response to a research study of the plurality of research studies matching the data associated with research studies of interest to the user. In other examples, the notification is displayed on the user device of the user as an email, text, message, banner, or badge, and wherein the notification comprises a selectable link that causes an authorization to be transmitted to the server granting access to the user's data by an entity conducting the research study of the plurality of research studies.

In some examples, the process may further include receiving, before receiving the authorization from the user to provide access to at least a portion of the user's wellness data, the user's wellness data; and storing the user's wellness data in the database of wellness data. In other examples, the method may further include receiving, before storing the user's wellness data in the database of wellness data, authorization from the user to include the user's wellness data in the database of wellness data.

Systems and non-transitory computer-readable storage media for performing these processes are also provided.

DETAILED DESCRIPTION

In the following description of the disclosure and examples, reference is made to the accompanying drawings in which it is shown by way of illustration specific examples that can be practiced. It is to be understood that other examples can be practiced and structural changes can be made without departing from the scope of the disclosure.

The present disclosure relates to receiving and sharing wellness data. The wellness data can be received by a user device from any number of sensors external or internal to the user device, from a user manually entering the wellness data, or from other users or entities. The user device can securely store the wellness data on the user device and transmit the wellness data to be stored on a remote registry database. A user of the device can share some or all of the wellness data stored in the registry database with research entities conducting research studies.

System Overview

Figure 1A:
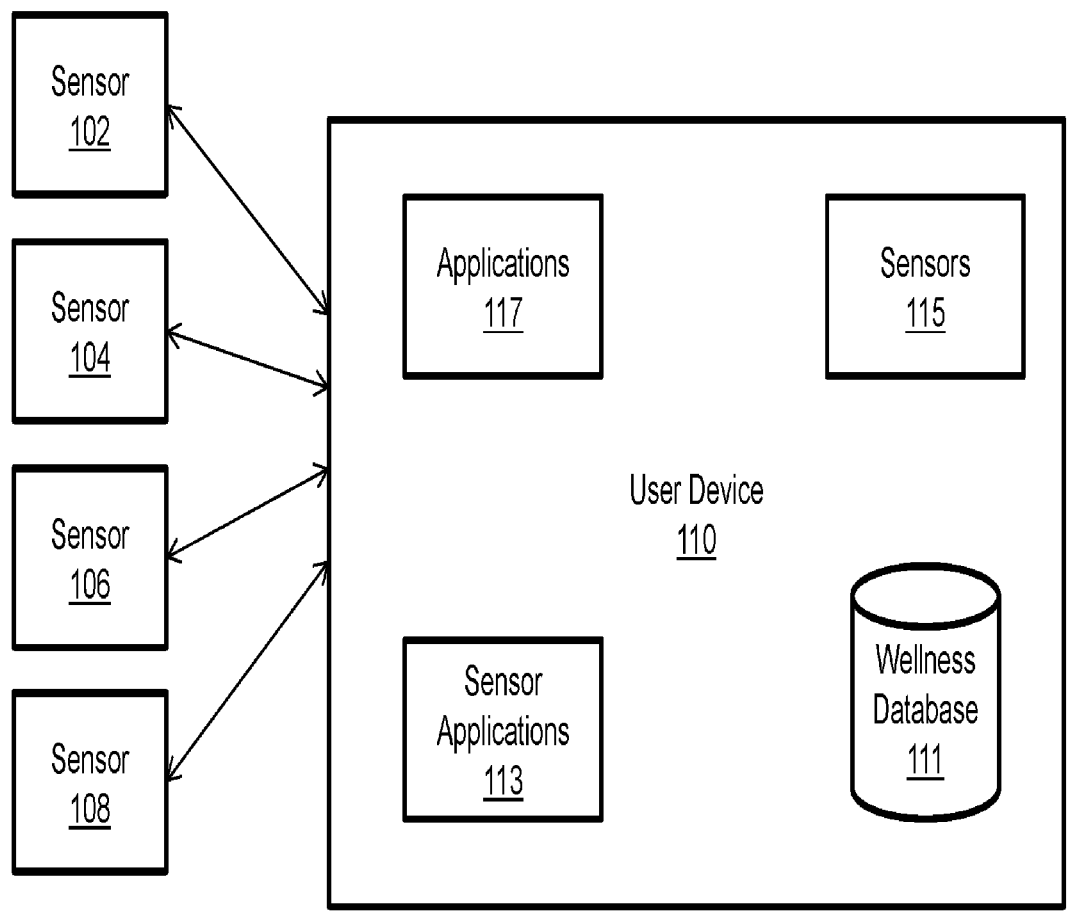
FIG. 1A illustrates a block diagram of an example system for receiving wellness data according to various examples.

FIG. 1 illustrates an example system 100A for receiving wellness data. As mentioned above, wellness data can include, but is not limited to, any type of data associated with a person's health, such as their weight, heart rate, blood pressure, blood glucose level, medication compliance, activity level, or the like. System 100A can be used to collect wellness data associated with a user, store the wellness data and present the wellness data to the user in useful ways. System 100A can further be used to collect non-wellness data along with wellness data, correlate the non-wellness data with the wellness data, and display the non-wellness data with the wellness data.

System 100A can include one or more user devices 110 including any electronic device, such as a mobile phone, tablet computer, desktop computer, laptop computer, PDA, or the like. User device 110 can include an operating system and a wellness database 111 for securely storing wellness or non-wellness data along with associated metadata, such as the time the data was recorded, type of data, device used to record the data, user associated with the data, and the like. User device 110 can further include application programming interfaces (APIs) with access controls for storing data in the wellness database 111 and for accessing data stored in the wellness database 111.

User device 110 can be configured to receive wellness or non-wellness data from various sources and can store the received data in the wellness database. For example, user device 110 can be configured to receive wellness or non-wellness data from sensors 102, 104, 106, and 108. These sensors can include any type of sensor capable of obtaining wellness data, such as a biometric sensor, activity tracker, or the like. For example, sensors 102, 104, 106, and 108 can include, but are not limited to, a scale, blood pressure cuff, blood glucose monitor, electrocardiogram, step counter, gyroscope, accelerometer, SpO2 sensor, respiration sensor, posture sensor, stress sensor, photoplethysmogram, galvanic skin response sensor, temperature sensor, asthma inhaler, or the like. Sensors 102, 104, 106, and 108 can also include other types of sensors, such as audio sensors, ambient light sensors, electromagnetic sensors, touch sensors, capacitive sensors, and the like, for obtaining non-wellness data, such as situational data, temporal data, personal data, contact data, and the like data. In some examples, each sensor can be a separate device, while, in other examples, any combination of two or more of the sensors can be included within a single device. For example, the gyroscope, accelerometer, photoplethysmogram, galvanic skin response sensor, and temperature sensor can be included within a wearable electronic device, such as a smart watch, while the scale, blood pressure cuff, blood glucose monitor, SpO2 sensor, respiration sensor, posture sensor, stress sensor, and asthma inhaler can each be separate devices. While specific examples are provided, it should be appreciated that other sensors can be used and other combinations of sensors can be combined into a single device.

Sensors 102, 104, 106, and 108 can be used to measure wellness or non-wellness data continuously, intermittently, periodically, or at any other desired frequency or interval of time. For example, sensors 102, 104, 106, and 108 can be used to obtain a single measurement or multiple measurements over a length of time. Additionally, sensors 102, 104, 106, 108 can be used to measure wellness or non-wellness data at any time or location desired by the user. Moreover, sensors 102, 104, 106, and 108 can be used with or without the supervision of a healthcare provider. For example, a user can use sensors 102, 104, 106, and 108 to obtain sensor measurements at home without the supervision of a medical professional.

In some examples, user device 110 can include software sensor applications 113 (e.g., third party applications) associated with each of sensors 102, 104, 106, and 108 for interfacing with the sensors to allow user device 110 to receive the wellness or non-wellness data. In these examples, the applications 113 can use the device's APIs to store the wellness or non-wellness data in the wellness database 111 of user device 110. In some examples, the software sensor applications 113 can be Apps and device 110 can be a smart phone, tablet computer, or the like. It should be understood that "third party" can correspond to an entity different than the manufacturer of device 110 and/or the entity that created and/or maintains the operating system of device 110. In these instances, third party applications and their corresponding sensors can communicate and function within the operating system of device 110 according to a predefined device protocol associated with device 110.

The applications 113 can similarly use the device's APIs to access data stored in the wellness database 111. In other examples, user device 110 can be configured to share one or more communication formats with sensors 102, 104, 106, and 108 to allow user device 110 to receive and interpret the wellness or non-wellness data from the sensors. The received data can then be stored in the wellness database 111 of user device 110.

User device 110 can further receive wellness or non-wellness data from its own wellness or non-wellness data sensors 115, such as a GPS sensor, clock, gyroscope, accelerometer, or the like, from a user interacting with user device 110, from another entity, such as a physician, or from other non-sensor sources. For example, using the device's APIs, wellness or non-wellness data can be received from applications 117 on user device 110, such as a clock application, a calendaring application, a gaming application, an application from a healthcare provider, a messaging application, or the like. The wellness or non-wellness data from the applications 117 can originate from a user interacting with the applications, a remote database (e.g., database for a medical website), a healthcare provider institution (e.g., via the institution's App), or the like. In these examples, the usage of the application 117 (e.g., how long you play a video game application, when you play the video game, number of times interacting with a stock application, number of times interacting with a social networking application, length of time interacting with a social networking application, etc.), usage of user device 110 (e.g., length of time on the phone or number of text messages sent as determined from a phone payment application, time spent browsing the Internet as determined from the device's browser, etc.), time spent listening to music as determined from a music or streaming radio application, time spent using a remote application for controlling a television, amount of time or money spent on shopping websites, time spent on pornographic websites (e.g., to identify addictions), weather data from a weather application (e.g., to determine how weather affects a user's health), type of events occurring in the user's life as determined from a calendar (e.g., meetings, birthdays, holidays, etc.), interactions with certain people as determined from a contact list and/or calendar application and/or a messaging application and/or phone of user device 110, or the like, can be received by user device 110 and stored in the wellness database 111.

In some examples, default or user-selected settings can be provided to restrict the access that at least one application (e.g., at least one of applications 113 and 117) on user device 110 has to the wellness database 111 of user device 110 (for both storage and retrieval purposes) and to the sensor data generated by sensors 115 within user device 110 and/or sensor data generated by sensors 102, 104, 106, and 108. For example, an application for tracking a user's running sessions can be granted access to the data generated by the GPS sensor of user device 110, but can be prevented from accessing the user's blood pressure data stored in the wellness database 111. In some examples, an entity other than the owner of user device 110 can set the authorization settings for various applications on user device 110. For example, the manufacturer of user device 110 and/or the entity that created and/or maintains the operating system of user device 110 can evaluate the applications to determine if they should be given access to the user's wellness data and/or sensor data generated or received by user device 110. In some examples, these settings can be overridden by the user.

Figure 1B:
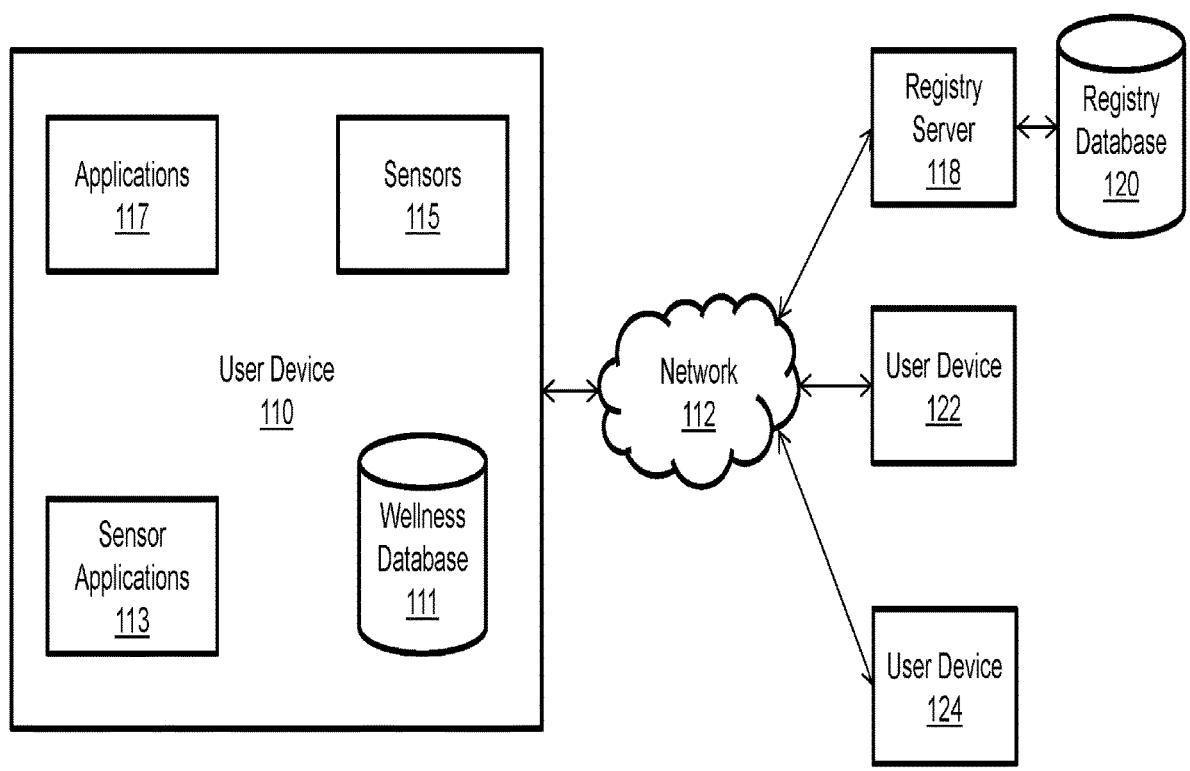
FIG. 1B illustrates a block diagram of an example system for sharing wellness data according to various examples.

FIG. 1B illustrates system 100B for sharing user wellness data. Referring to FIG. 1B, system 100B can include registry server 118 communicatively coupled to user device 110 via network 112, which can include the Internet, an intranet, or any other wired or wireless public or private network. In the case in which a user of device 110 wishes to do so by opting into data sharing, user device 110 can be configured to securely transmit the received wellness or non-wellness data and associated metadata stored in wellness database 111 to registry server 118 for storage in registry database 120. The user of device 110 can opt into sharing some or all of their wellness and non-wellness data. For example, a user can choose to share all wellness and non-wellness data, only certain types of wellness or non-wellness data, or a subset of a type of wellness or non-wellness data. Registry database 120 can be used to store wellness or non-wellness data associated with a large number of users for the purpose of providing researchers with access to a large volume of wellness data that would not otherwise be available to them. For privacy reasons, registry database 120 can be configured to securely store a user's wellness or non-wellness data anonymously (e.g., without identifying and/or personal information about the user, such as a legal name, username, time and location data, or the like). Additionally, the wellness or non-wellness data can only be included within registry database 120 (or, alternatively, made searchable) with the user's authorization by, for example, opting into a data sharing program. Absent such an authorization, the user's wellness or non-wellness data may be excluded from registry database 120 (e.g., by not storing the user's wellness or non-wellness data in registry database 120). In some examples, the identifiers for users in registry database 120 can be different for each querying entity. For example, a first research entity may be provided with an identifier having a value of 37 for one of the users in registry database 120, while a second research entity may be provided with an identifier having a value of 82 for the same user. This can be done to prevent collusion between researchers. The operation of registry database 120 will be discussed in greater detail below with respect to FIGS. 2-3.

System 100B can further include any number of other user devices 122 and 124 coupled to network 112. In some examples, user devices 122 and 124 can be operated by the same user as user device 110. In these instances, the user can transmit their wellness or non-wellness data to registry server 118 for storage in registry database 120 using appropriate credentials. Additionally, in some examples, a user's wellness data can by synced between registry database 120 and one or more of user devices 110, 122, and 124. In other examples, the user of user devices 122 and 124 can be a person that is different than the user of user device 110. In these examples, the users of devices 122 and 124 cannot access the wellness or non-wellness data of the user of user device 110 within registry database 120. While not shown, it should be appreciated that many other user devices can be coupled to registry server 118 through network 112 to collect and store wellness or non-wellness data for other users in a manner similar to that described above.

Registry Database

As discussed above, registry database 120 can be used to store wellness or non-wellness data from a large number (e.g., millions) of users upon their authorization. Researchers can then request access to the wellness or non-wellness data for the purpose of performing medical research. Providing researchers with a reliable stream of constantly updating sensor data for millions of users can allow the researchers to conduct faster and more accurate studies.

For privacy reasons, different levels of authorization can be used to control access to the data contained in registry database 120. Once a user authorizes some or all of their wellness or non-wellness data to be accessed by adding their data to registry database 120, the user or another entity, such as a review board associated with registry database 120, can provide researchers or querying entities with various levels of authorization to access the registry data. In a first level of authorization, a querying entity can be given access to certain types of wellness data, such as blood pressure and height, for all registry participants. Under this level of authorization, the querying entity's access to data contained in registry database 120 can be limited to the types of data specified by the authorization. In some examples, the owner/operator of registry database 120 can perform queries submitted by querying entities to further limit the access the researchers have to the wellness or non-wellness data contained in registry database 120.

In a second level of authorization, a querying entity can be given limited access to data that allows the querying entity to identify potential study participants, generate population level histograms, or the like. Under this level of authorization, if the querying entity desires more detailed information about specific user records, then an explicit authorization from the associated users may be required. The authorization from the user can be received in response to a request made by the querying entity and sent to the user by registry server 118. The request can include a link or other selectable element that can allow the user to quickly opt-in to the study, thereby granting access to the user's wellness or non-wellness data. The link or other selectable element can be part of a user interface associated with an App from applications 113 or 117 that can be associated with one or more types of wellness, non-wellness, or sensor data.

Users can also proactively provide explicit authorization to some or all of their wellness data to selected research studies. For example, users can search for certain studies by searching, using a computing device (e.g., user device 110), through a displayed list of research studies stored by registry server 118, selecting a research study of interest from the list via a user input to the computing device, and making a selection by providing a user input to the computing device to opt-in to participate in the study. This authorization can then be transmitted from user device 110 to registry server 118 via network 112, thereby granting access to the research entity performing the research study of interest. In another example, a user can provide registry server 118 with information about the type(s) of research studies that may be of interest to the user. For example, the user may select from a displayed list of types of illnesses, types of data, and the like (e.g., high blood pressure, colon cancer, heart disease, activity data, and the like), and select from the displayed list via a user input to the computing device, the type of illnesses studies that they are interested in participating in. Registry server 118 can monitor a current list of research studies being conducted to identify studies that match the user's preferences and can send notifications to potentially interested users via network 112 and user device 110. The notifications can be displayed on the user's device as an email, text, message, banner, badge, or the like, and can include a link or other selectable element that, when selected by the user, can allow the user to quickly opt-in to the study, thereby granting the entity associated with the study access to the user's wellness or non-wellness data.

In some examples, the querying entity can request additional data not contained in the registry database from the users. This request can be sent by the research entity or the owner/operator of the registry server (e.g., via registry server 118) to a device (e.g., user device 110) of the user. If the user agrees to participate, the user's registry identification can be revealed to the querying entity to allow the querying entity to combine the user's registry data with the requested additional data.

Figure 2:
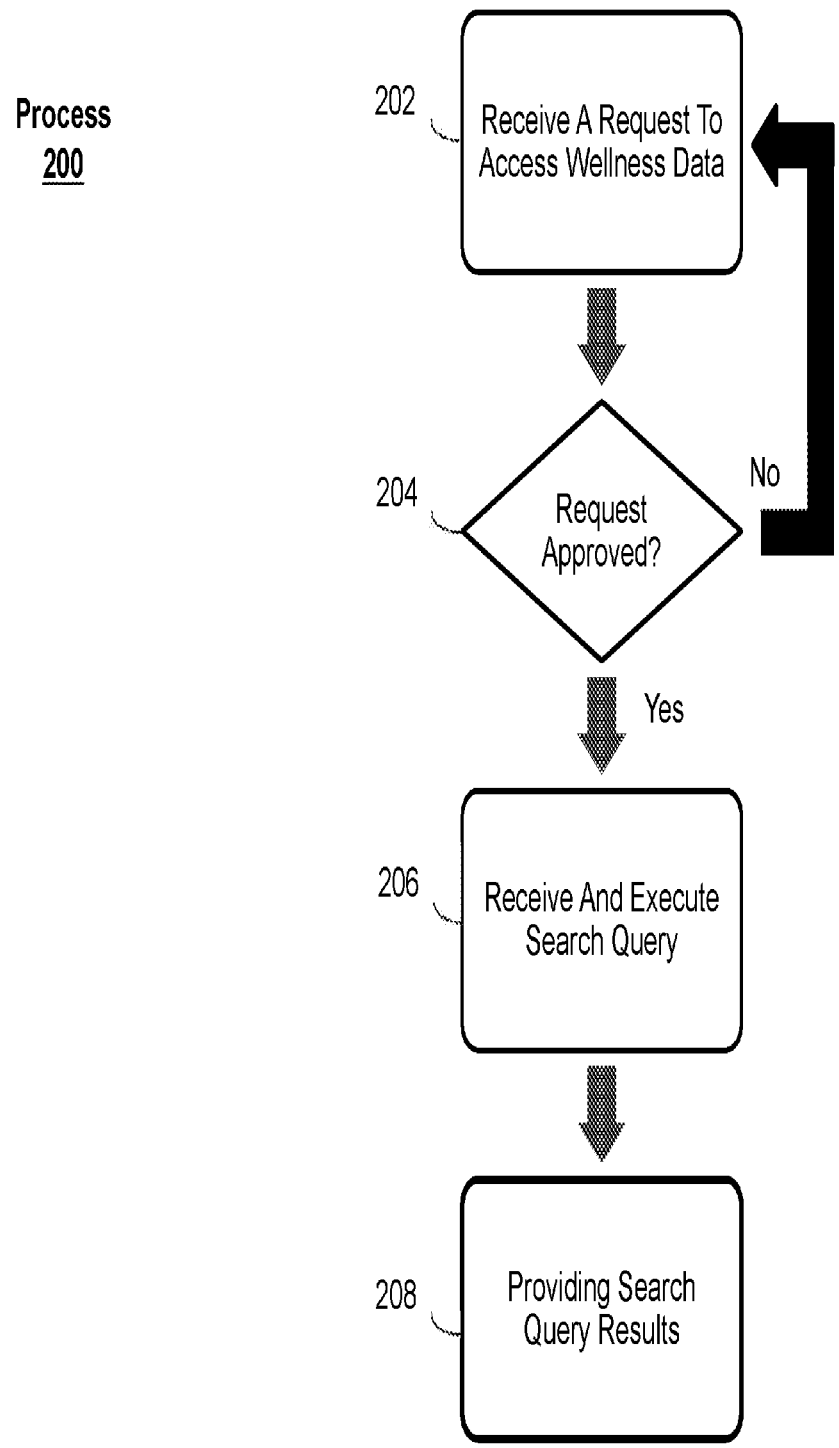
FIG. 2 illustrates an example process for performing search queries on a health registry according to various examples.
Figure 3:
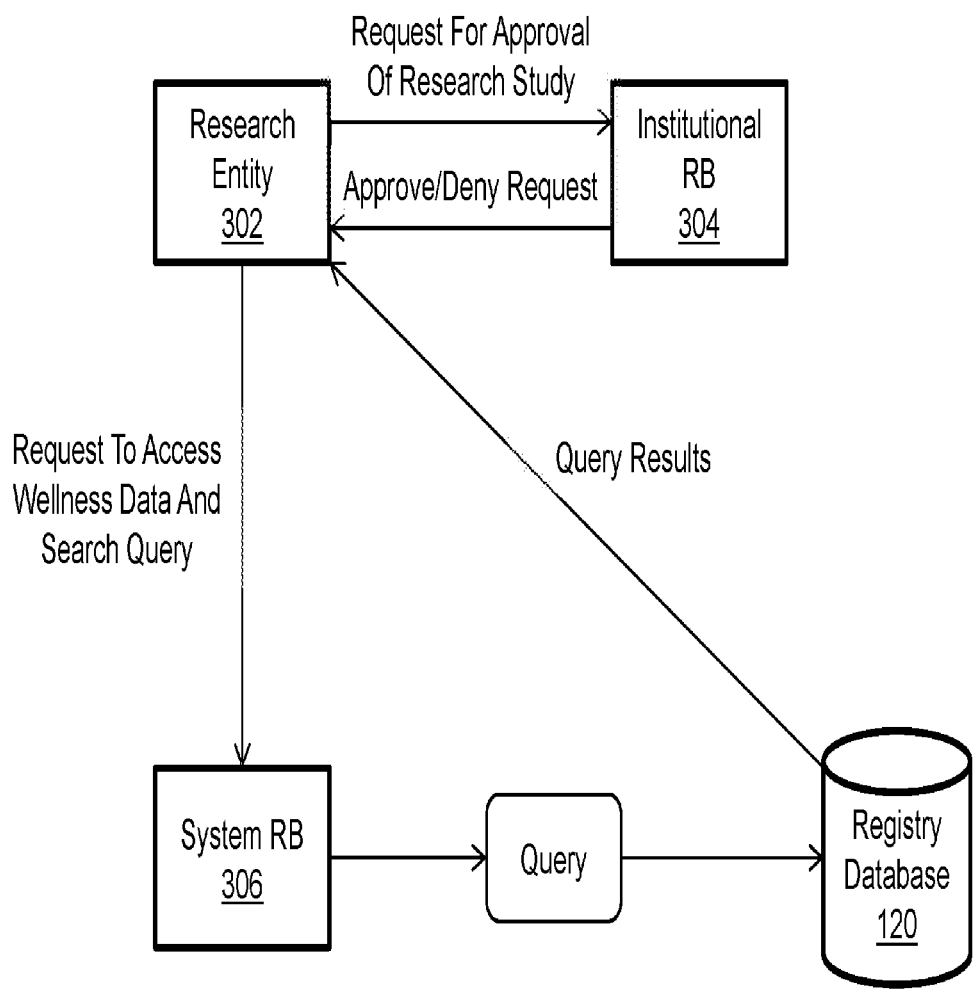
FIG. 3 illustrates a block diagram depicting an exemplary interaction between a research entity and a health registry using the process of FIG. 2.

FIG. 2 illustrates an example process that can be used to perform queries on registry database 120. At block 202, an owner or operator of a registry database similar or identical to database 120 can receive a request to access wellness or non-wellness data stored in the registry. The request can be received by registry server 118 via network 112 or can be received through another communication medium (e.g., paper application request, telephone, in-person, or the like). The requesting research entity can, in some examples, be a part of an institution, such as a university, company, or the like, and can first request and receive approval for performing the research study from an internal review board. To illustrate, FIG. 3 shows a block diagram depicting an example query interaction 300 that can occur when performing queries on registry database 120 using process 200. As shown, research entity 302 can submit a request for approval of a research study to an institutional review board 304. The institutional review board 304 can review the merits of the study and either approve or deny the request. If approved, the research entity can submit a request to access one or more types of approved data contained in registry database 120. This request can be received by the owner/operator of registry database 120 (e.g., system review board 306).

Referring back to FIG. 2, at block 204, the owner/operator of registry database 120 can evaluate the request to determine if access to the wellness or non-wellness data should be granted. This can include evaluating the entity submitting the request, the proposed research study, the type or amount of data requested, or the like. If the request is denied, the process can return to block 202 where additional requests for access to the wellness or non-wellness data can be received from the same or other research entities. If, however, the request is granted, the process can proceed to block 206.

At block 206, a search query to be performed on the registry database can be received. The request can include any number of search parameters related to the types of wellness or non-wellness data and the metadata stored in the registry database. The search query can be evaluated to determine if it violates any search query rules (if any exist). For example, search queries can be rejected if they would too narrowly characterize the user, such that the user's identity can be determined or inferred. If the search query is approved, the owner/operator of the registry database can execute the search query on the registry database. In some examples, before the search query can be executed on users' data in the registry data, authorizations from the users to allow their data to be searchable can be received. In these examples, if no authorization is received from a user, the search query request to search the user's data can be denied and the search query may not be executed on the user's data. To illustrate, referring again to FIG. 3, research entity 302 can submit a query request to system review board 306 for a query to be run on registry database 120. If approved by system review board 306, the query can be executed on the wellness and non-wellness data in the registry database of users that provided authorizations to allow their data to be searchable.

Referring back to FIG. 2, at block 208, the results of the search query can be provided to the requesting research entity. The results can include any desired amount of wellness or non-wellness data resulting from the search query. For example, the results can include only a list of anonymous identifiers for users that match the search query. Depending on the authorization settings, the research entity can then request that notifications be sent to the matching users, asking them if they would like to participate in the research study. In other examples, some or all of the wellness or non-wellness data associated with matching users can be provided to the requesting research entity. The amount of data can depend on the preferences of the owner/operator of the registry server, level of authorization provided by the users, terms of the agreement between the research entity and the owner/operator of registry server 118, or the like. In some examples, if authorized by the user, the research entity can request additional data not contained in the registry database from the users. This request can be sent by the research entity or the owner/operator of the registry server (e.g., via registry server 118) to a device (e.g., user device 110) of the user.

To illustrate, referring again to FIG. 3, the search query can be performed on registry database 120 and the results of the query can be transmitted to research entity 302. While shown as being sent directly from registry database 120 to research entity 302, it should be appreciated that a server, such as registry server 118, can be used to transmit the query results to research entity 302.

In some examples, before or after any blocks of process 200, the contents of the registry database can be updated. In these examples, the wellness or non-wellness data from one, two, or more users can be received by the registry's server (e.g., registry server 118) from the device(s) of the user(s). For example, the wellness or non-wellness data can be stored on wellness database 111 of user device 110 and can be transmitted to registry server 118 via network 112. In response to receiving the wellness or non-wellness data, the registry database can be updated to include the received wellness or non-wellness data. In some examples, user devices of users that store wellness or non-wellness data in the registry database can transmit updates to the users' wellness or non-wellness data periodically, intermittently, continuously, or at any other desired interval of time.

In some examples, user device 110 or another computing device can display an interface for searching for research studies in which a user can participate. The interface can include a list of one or more possible research studies in which a user can participate. The interface can allow a user to search for particular research studies based on any desired criteria, such as location, entity conducting the study, the subject of the study, or the like. In some examples, the interface can include one or more recommended studies that the user is particularly qualified to participate in based on the user's wellness data stored in the registry. For example, if the user's wellness data in registry database 120 indicates that the user is a male with brown hair, diabetes, and over the age of 50, the research study search interface can recommend diabetes research studies that are looking for participants having those traits. In some examples, the interface can include a button or other selectable element that a user can select to make their wellness data in registry database 120 available for use in the selected research study.

Figure 4:
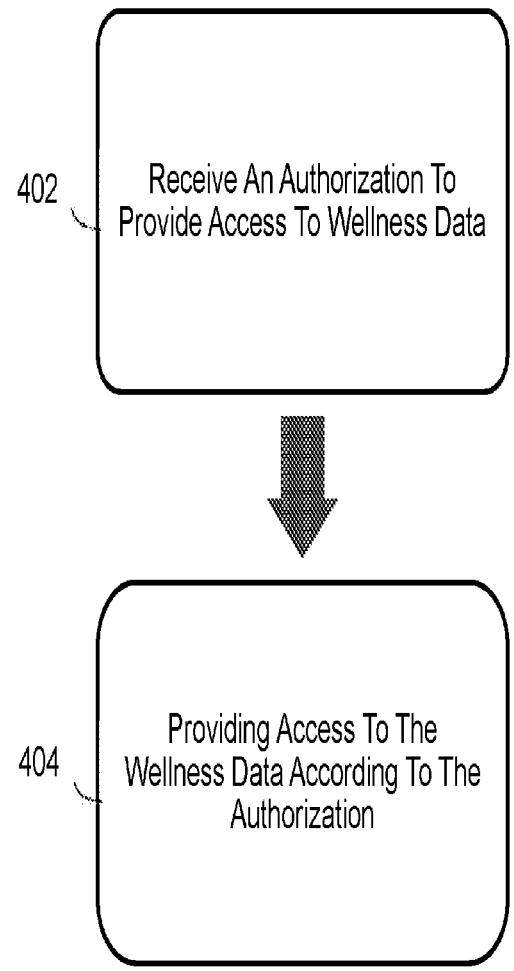
FIG. 4 illustrates an example process for managing access to a health registry according to various examples.

FIG. 4 illustrates an exemplary process 400 for managing access to a health registry according to various examples. At block 402, an authorization to provide access to wellness or non-wellness data in a registry database similar or identical to registry database 120 can be received. In some examples, the request can be received by a server (e.g., registry server 118) associated with the registry database from a computing device similar or identical to user device 110, 122, or 124. The authorization can include an indication of a user's desire to opt in to a sharing program.

In one example, the authorization can indicate that the user authorizes research entities to perform queries (e.g., using process 200) on some or all of the user's data. For example, the authorization can indicate that all of the user's data can be queried, certain types of the user's data can be queried, or a subset of a type of the user's data can be queried.

In another example, the authorization can be received in response to a request made by the querying entity and sent to the user by the registry server. The request can include a link or other selectable element that can allow the user to quickly opt-in to the study, thereby granting access to the user's wellness or non-wellness data. The link or other selectable element can be part of a user interface associated with an App from applications (e.g., applications 113 or 117) that can be associated with one or more types of wellness, non-wellness, or sensor data.

In other examples, the authorization can include an explicit authorization to some or all of the user's data to selected research studies. For example, the user can search for certain studies by searching, using the computing device, through a displayed list of research studies stored by the registry server, selecting a research study of interest from the list via user input to the computing device, and making a selection by providing a user input to the computing device to opt-in to participate in the research study. An authorization for an entity associated with the selected research study to access the user's data can be transmitted to the registry server.

In another example, the user can provide the registry server with information about the type(s) of research studies that may be of interest to the user. For example, the user may select from a displayed list of types of illnesses, types of data, and the like (e.g., high blood pressure, colon cancer, heart disease, activity data, and the like) and select from the displayed list via a user input to the computing device, the type of illnesses studies they are interested in participating in. The registry server can monitor a current list of research studies being conducted to identify studies that match the user's preferences and can send notifications to potentially interested users via a network (e.g., network 112) and the user's computing device. The notifications can be displayed on the user's device as an e-mail, a text, a message, a banner, a badge or the like and can include a link or other selectable element that, when selected by the user, can allow the user to quickly opt-in to the study, thereby granting the entity associated with the study access to the user's wellness or non-wellness data. In response to the user's selection, an authorization granting the entity access to the user's wellness data can be transmitted to the registry server.

At block 404, access to the wellness and non-wellness data in the registry server can be provided based on the authorization received at block 402. In some examples, this can include allowing research entities to query the data using, for example, process 200. In other examples, this can include providing a particular entity identified in the authorization with access to the user's data. If, however, no authorization was received to provide access to a user's data at block 402, any requests to query or access the user's data can be denied.

Figure 5:
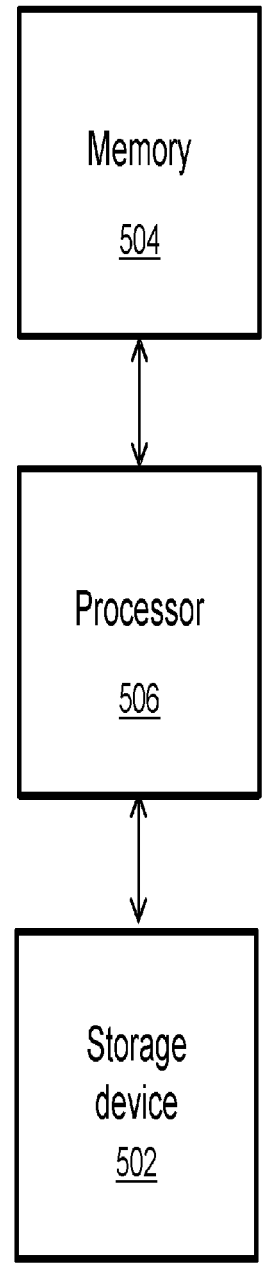
FIG. 5 illustrates an example computing system for receiving and sharing wellness data according to various examples.

One or more of the functions relating to receiving and sharing wellness data can be performed by a system similar or identical to system 500 shown in FIG. 5. System 500 can include instructions stored in a non-transitory computer readable storage medium, such as memory 504 or storage device 502, and executed by processor 506. The instructions can also be stored and/or transported within any non-transitory computer readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer readable storage medium" can be any medium that can contain or store the program for use by or in connection with the instruction execution system, apparatus, or device. The non-transitory computer readable storage medium can include, but is not limited to, an electronic, magnetic, optical, electromagnetic, infrared, or semiconductor system, apparatus or device, a portable computer diskette (magnetic), a random access memory (RAM), a read-only memory (ROM), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The instructions can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

In some examples, system 500 can be included within user device 110 or registry server 118. Processor 506 can be configured to perform process 200 or 400. It is to be understood that the system is not limited to the components and configuration of FIG. 5 but can include other or additional components in multiple configurations according to various examples.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the appended claims.

What is claimed is:

1. A computer-implemented method comprising:
   receiving, from a plurality of user devices, wellness data authorized for storage to a database of wellness data;
   storing the wellness data in the database of wellness data;
   receiving, from a research entity, a request to access the database of wellness data;
   approving the request to access the database of wellness data;
   receiving, from the research entity, a request to perform a search query on the database of wellness data;
   determining whether a user's identity can be determined or inferred from the search query;
   in accordance with a determination that a user's identity can be determined or inferred from the search query, rejecting the search query; and
   in accordance with a determination that the search query is approved:
      performing the search query according to search query rules; and
      transmitting results of the search query to the research entity.

2. The computer-implemented method of claim 1, wherein the wellness data is associated with a plurality of users, and wherein an authorization to include the wellness data in the database of wellness data was received from each of the plurality of users prior to the wellness data being stored in the database of wellness data.

3. The computer-implemented method of claim 1, further comprising:
   receiving wellness data of two or more users; and
   storing the received wellness data of the two or more users in the database of wellness data.

4. The computer-implemented method of claim 3 further comprising receiving, before storing the received wellness data of the two or more users in the database of wellness data, an authorization from each of the two or more users to include the received wellness data in the database of wellness data.

5. The computer-implemented method of claim 1, further comprising:
   receiving wellness data of two or more users; and
   excluding the received wellness data of the two or more users from the database of wellness data absent an authorization from each of the two or more users that their wellness data is to be included in the database of wellness data.

6. The computer-implemented method of claim 1, further comprising receiving wellness data of two or more users, wherein the wellness data of each of the two or more users is received from a wellness database located on a user device of each user.

7. The computer-implemented method of claim 6, further comprising updating the database of wellness data by receiving one of intermittent and continuous updates from the wellness database located on each user's user device.

8. The computer-implemented method of claim 1, wherein the database of wellness data comprises metadata associated with the wellness data, wherein the metadata comprises a time the wellness data was recorded, a type of the wellness data, and a device used to record the wellness data.

9. The computer-implemented method of claim 1, wherein the database of wellness data comprises wellness data from a plurality of users.

10. The computer-implemented method of claim 9, further comprising receiving, prior to performing the search query, authorization from two or more users of the plurality of users to authorize their wellness data to be searchable.

11. The computer-implemented method of claim 9, further comprising denying the search query on wellness data from the plurality of users absent authorization that their wellness data is to be searchable.

12. The computer-implemented method of claim 1 wherein the wellness data is stored in the database of wellness data anonymously.

13. A non-transitory computer-readable storage medium storing one or more programs configured to be executed by one or more processors, the one or more programs including instructions for:

receiving, from a plurality of user devices, wellness data authorized for storage to a database of wellness data;
storing the wellness data in the database of wellness data;
receiving, from a research entity, a request to access the database of wellness data;
approving the request to access the database of wellness data;
receiving, from the research entity, a request to perform a search query on the database of wellness data;
determining whether a user's identity can be determined or inferred from the search query;
in accordance with a determination that a user's identity can be determined or inferred from the search query, rejecting the search query; and
in accordance with a determination that the search query is approved:
performing the search query according to search query rules; and
transmitting results of the search query to the research entity.

14. The non-transitory computer-readable storage medium of claim 13, wherein the wellness data is associated with a plurality of users, and wherein an authorization to include the wellness data in the database of wellness data was received from each of the plurality of users prior to the wellness data being stored in the database of wellness data.

15. The non-transitory computer-readable storage medium of claim 13, further comprising instructions for:
receiving wellness data of two or more users; and
storing the received wellness data of the two or more users in the database of wellness data.

16. The non-transitory computer-readable storage medium of claim 15, further comprising instructions for:
receiving, before storing the received wellness data of the two or more users in the database of wellness data, an authorization from each of the two or more users to include the received wellness data in the database of wellness data.

17. The non-transitory computer-readable storage medium of claim 13, further comprising instructions for:
receiving wellness data of two or more users; and
excluding the received wellness data of the two or more users from the database of wellness data absent an authorization from each of the two or more users that their wellness data is to be included in the database of wellness data.

18. The non-transitory computer-readable storage medium of claim 13, further comprising instructions for:
receiving wellness data of two or more users, wherein the wellness data of each of the two or more users is received from a wellness database located on a user device of each user.

19. The non-transitory computer-readable storage medium of claim 18, further comprising instructions for:
updating the database of wellness data by receiving one of intermittent and continuous updates from the wellness database located on each user's user device.

20. The non-transitory computer-readable storage medium of claim 13, wherein the database of wellness data comprises metadata associated with the wellness data, wherein the metadata comprises a time the wellness data was recorded, a type of the wellness data, and a device used to record the wellness data.

21. The non-transitory computer-readable storage medium of claim 13, wherein the database of wellness data comprises wellness data from a plurality of users.

22. The non-transitory computer-readable storage medium of claim 21, further comprising instructions for:
receiving, prior to performing the search query, authorization from two or more users of the plurality of users to authorize their wellness data to be searchable.

23. The non-transitory computer-readable storage medium of claim 21, further comprising instructions for:
denying a search query on wellness data from the plurality of users absent authorization that their wellness data is to be searchable.

24. The non-transitory computer-readable storage medium of claim 13 wherein the wellness data is stored in the database of wellness data anonymously.

25. An electronic device, comprising:
one or more processors;
a memory; and
computer-executable instructions, wherein the computer-executable instructions are stored in the memory and configured to be executed by the one or more processors, the computer-executable instructions including instructions for:
receiving, from a plurality of user devices, wellness data authorized for storage to a database of wellness data;
storing the wellness data in the database of wellness data;
receiving, from a research entity, a request to access the database of wellness data;
approving the request to access the database of wellness data;
receiving, from the research entity, a request to perform a search query on the database of wellness data;
determining whether a user's identity can be determined or inferred from the search query;
in accordance with a determination that a user's identity can be determined or inferred from the search query, rejecting the search query; and
in accordance with a determination that the search query is approved:
performing the search query according to search query rules; and
transmitting results of the search query to the research entity.

26. The electronic device of claim 25, wherein the wellness data is associated with a plurality of users, and wherein an authorization to include the wellness data in the database of wellness data was received from each of the plurality of users prior to the wellness data being stored in the database of wellness data.

27. The electronic device of claim 25, wherein the computer-executable instructions further include instructions for:
receiving wellness data of two or more users; and
storing the received wellness data of the two or more users in the database of wellness data.

28. The electronic device of claim 27, wherein the computer-executable instructions further include instructions for:
receiving, before storing the received wellness data of the two or more users in the database of wellness data, an authorization from each of the two or more users to include the received wellness data in the database of wellness data.

29. The electronic device of claim 25, wherein the computer-executable instructions further include instructions for:
receiving wellness data of two or more users; and
excluding the received wellness data of the two or more users from the database of wellness data absent an authorization from each of the two or more users that their wellness data is to be included in the database of wellness data.

30. The electronic device of claim 25, wherein the computer-executable instructions further include instructions for:
receiving wellness data of two or more users, wherein the wellness data of each of the two or more users is received from a wellness database located on a user device of each user.

31. The electronic device of claim 30, wherein the computer-executable instructions further include instructions for:
updating the database of wellness data by receiving one of intermittent and continuous updates from the wellness database located on each user's user device.

32. The electronic device of claim 25, wherein the database of wellness data comprises metadata associated with the wellness data, wherein the metadata comprises a time the wellness data was recorded, a type of the wellness data, and a device used to record the wellness data.

33. The electronic device of claim 25, wherein the database of wellness data comprises wellness data from a plurality of users.

34. The electronic device of claim 33, wherein the computer-executable instructions further include instructions for:
receiving, prior to performing the search query, authorization from two or more users of the plurality of users to authorize their wellness data to be searchable.

35. The electronic device of claim 33, wherein the computer-executable instructions further include instructions for:
denying a search query on wellness data from the plurality of users absent authorization that their wellness data is to be searchable.

36. The electronic device of claim 25, wherein the wellness data is stored in the database of wellness data anonymously.

* * * * *